US008677601B2

United States Patent
Millwee et al.

(10) Patent No.: US 8,677,601 B2
(45) Date of Patent: Mar. 25, 2014

(54) PROSTHETIC HEART VALVE, PROSTHETIC HEART VALVE ASSEMBLY AND METHOD FOR MAKING SAME

(75) Inventors: Billie J. Millwee, Fullerton, CA (US); Janice L. Shay, Lake Forest, CA (US); Carolyn Majkrzak, San Clemente, CA (US); Melissa Young, Cleveland Heights, OH (US); Tara S. Kupumbati, Irvine, CA (US)

(73) Assignee: Medtronic, Inc., Minneapolis, MN (US)

( * ) Notice: Subject to any disclaimer, the term of this patent is extended or adjusted under 35 U.S.C. 154(b) by 203 days.

(21) Appl. No.: 13/370,725

(22) Filed: Feb. 10, 2012

(65) Prior Publication Data

US 2012/0137521 A1 Jun. 7, 2012

Related U.S. Application Data

(63) Continuation of application No. 12/424,682, filed on Apr. 16, 2009, now Pat. No. 8,136,218.

(60) Provisional application No. 61/048,691, filed on Apr. 29, 2008.

(51) Int. Cl.
*B23P 17/00* (2006.01)

(52) U.S. Cl.
USPC ...................................................... 29/527.3

(58) Field of Classification Search
USPC .............. 29/527.3, 890.124, 460, 527.2, 428, 29/464, 468; 425/470; 264/299; 623/2.11–2, 13, 2.28, 900
See application file for complete search history.

(56) References Cited

U.S. PATENT DOCUMENTS

| | | | |
|---|---|---|---|
| 4,218,782 | A | 8/1980 | Rygg |
| 4,655,771 | A | 4/1987 | Wallsten |
| 4,692,164 | A | 9/1987 | Dzemeshkevich et al. |
| 4,758,151 | A | 7/1988 | Arru et al. |
| 5,163,955 | A | 11/1992 | Love et al. |
| 5,509,930 | A | 4/1996 | Love |
| 5,713,953 | A | 2/1998 | Vallana et al. |
| 6,136,023 | A | 10/2000 | Boyle |
| 6,491,511 | B1 | 12/2002 | Duran et al. |
| 6,641,609 | B2 | 11/2003 | Globerman |
| 6,656,219 | B1 | 12/2003 | Wiktor |
| 6,726,715 | B2 | 4/2004 | Sutherland |
| 6,773,455 | B2 | 8/2004 | Allen et al. |
| 7,141,064 | B2 | 11/2006 | Scott et al. |
| 2006/0206202 | A1 | 9/2006 | Bonhoeffer et al. |
| 2010/0018447 | A1 | 1/2010 | Holecek et al. |

FOREIGN PATENT DOCUMENTS

WO 2007/046000 A1 4/2007

OTHER PUBLICATIONS

Duran et al., "Aortic Valve Replacement with Freehand Autologous Preicardium", J. Thorac. Cardiovasc. Surg., 110:511-6 (1995).
Love et al., "Autologous Pericardinal Reconstruction of Semilunar Valves". J. Heart Valve Dis., 7(1):40-7 (1998).

*Primary Examiner* — John C Hong

(57) ABSTRACT

A method of forming a leaflet of a prosthetic valve includes placing a first piece of material on a working surface. A leaflet mold is placed on the first piece of material, and provides a outer peripheral shape comprising a curved portion. A second piece of material is placed over the first piece and the leaflet mold. The first and second pieces of material are stitched to one another along at least a portion of the curved portion of the leaflet mold. The leaflet mold is removed from first and second pieces of material.

12 Claims, 13 Drawing Sheets

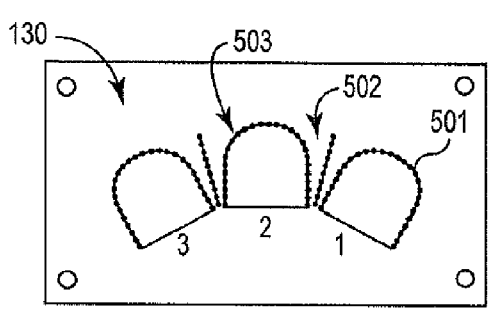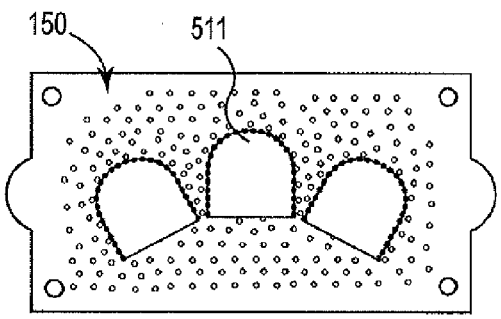
Fig. 18  Fig. 19
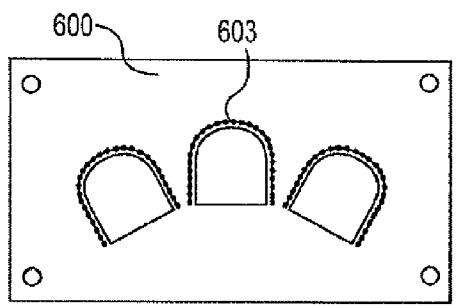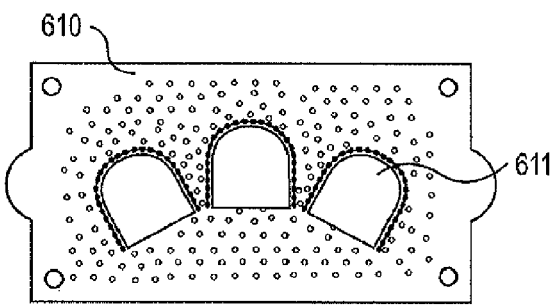
Fig. 20  Fig. 21
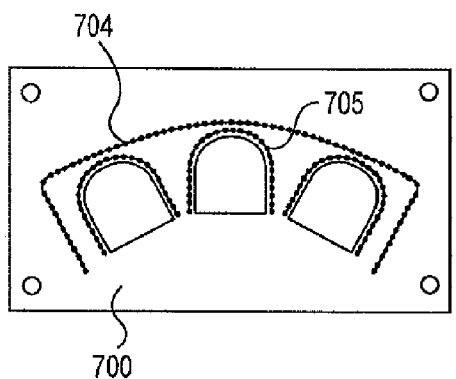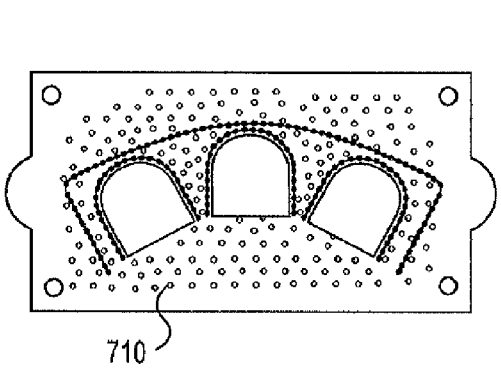
Fig. 22  Fig. 23

PROSTHETIC HEART VALVE, PROSTHETIC HEART VALVE ASSEMBLY AND METHOD FOR MAKING SAME

CROSS-REFERENCE TO RELATED APPLICATIONS

The present application is a continuation of U.S. application Ser. No. 12/424,682, filed Apr. 16, 2009, and titled "Prosthetic Heart Valve, Prosthetic Heart Valve Assembly and Method for Making Same" that claims priority to U.S. Provisional Application No. 61/048,691, filed Apr. 29, 2008, and titled "Prosthetic Heart Valve, Prosthetic Heart Valve Assembly and Method for Making Same", the entire contents of each of which are incorporated herein by reference in their entirety.

TECHNICAL FIELD

The present invention relates generally to devices and methods for making prosthetic heart valves. More specifically, the invention relates to devices and methods to shape and/or mold heart valves from sheets of material, and methods to durably attach a tissue valve to a stent.

BACKGROUND

Recently, there has been increasing interest in minimally invasive and percutaneous replacement of heart valves in a patient. One type of valve that can be used is referred to as a prosthetic heart valve. Prosthetic heart valves can be constructed from a variety of naturally occurring tissue, such as mammalian tissue, which may include either human tissue including autologous tissue or cadaverous (homologous) tissue, or animal tissue, which would be heterologous tissue.

Autologous, homologous and heterologous tissue can be shaped using molds to more closely resemble a functional natural valve. However, there exists a need in the art for additional shaping and molding techniques. In particular, there is a need for methods of incorporating a shaped prosthetic valve with a stent or other type of frame, since conventional designs and methods often produce a stented valve that has concentrated stresses at the points where the leaflets are attached to the stent frame. In some cases, the stents are rigid as compared to the flexible material from which the leaflets of the tissue valve are made, such that the repetitive flexing motion of the leaflets can create stress concentrations at the points where the tissue valve is attached to the stent. These stress concentrations can eventually lead to tearing of the tissue, valve leakage, and/or failure of the heart valve. Thus, there is a continued need in the art for devices and methods to shape and/or mold heart valves, and for methods to durably attach a tissue valve to a stent and/or to distribute the stresses away from the attachment and seam areas for bioprosthetic heart valves, and methods of using the same.

SUMMARY

The present invention provides molds for shaping at least one leaflet of a prosthetic heart valve (e.g., aortic, pulmonary, triscuspid, or mitral replacement valves), and methods for fabricating a prosthetic heart valve and prosthetic heart valve assembly using the same. In one aspect of the invention, the molds or fixtures used for forming leaflets allow for selective exposure of solution to certain portions of the tissue during the fixation process. That is, one surface of the tissue used for the leaflets is directly exposed to the fixation solution since there is no portion of the fixture or mold that is in contact with the exposed or outwardly facing surface of the leaflet tissue. In addition, the surface of the mold or fixture that is in contact with one surface of the tissue (i.e., the side of the tissue that is opposite the outwardly facing surface) is relatively smooth in order to prevent impressions or other tissue damage. In the area of the skirt or area surrounding the leaflets, neither side of the tissue will be directly exposed to the fixation solution. Instead, small holes or channels in the fixture or mold will allow movement of solution to the tissue. In order to accomplish this, a top plate and a bottom plate are provided, wherein these plates are able to hold the tissue material in place in the skirt area and also impart a tension on the material that can hold the portion of the material that will become the leaflet(s) in place while not actually contacting both sides of the leaflet portion(s) of the tissue. However, the holes or channels in the fixture provide the necessary structures for delivery of fixation solution to the skirt portion of the tissue material. In this way, the tissue material can be effectively clamped in place while delivering the necessary amount of fixation solution to the various portions of the tissue material. In another aspect of the invention, one of the components of a fixturing assembly includes built-in stitching guides that provide commissure protection for the valve. The fixtures of the assembly further provide a way of holding commissure protection features in place during assembly, such as independent support structures that will be sewn into the commissures. In another aspect of the invention, one of the components of a fixturing assembly provide the technician who is assembling the valve with a 2-dimensional plane and pattern for joining the valve skirt to the leaflets. That is, one or more of the plates of the fixture assembly will be provided with a cuff sewing guide that dictates the location of the assembly seam and the distance that the stitches will be placed from one another. Such a sewing guide can improve the quality and consistency of stitching, along with making the assembly process quicker. In yet another aspect of the invention, one or more of the plates of the fixture can provide a template or leaflet sewing guide for sewing stitches around each of the leaflets. As with the cuff sewing guide, the leaflet sewing guide would provide the technician with a 2-dimensional plane and pattern for assembly and stitching of each of the leaflets in a quick, consistent, and high-quality manner.

In another aspect of the invention, the fixation of tissue into leaflets for a valve is accomplished in 3-dimensions rather than 2-dimensions, which provides advantages when assembling a 3-dimensional valved stent. With such a 3-dimensional fixture structure, the leaflets can be sewn into a shape that more closely matches that of a 3-dimensional patient anatomy. In addition, the use of such a structure can eliminate or minimize any inconsistencies that may occur when translating a 3-dimensional valve design into a 2-dimensional fixture pattern and then again to a 3-dimensional pattern.

In yet other aspects, methods of forming a leaflet of a prosthetic valve are provided and include placing a first piece of material on a working surface. A leaflet mold is placed on the first piece of material, and provides an outer peripheral shape comprising a curved portion. A second piece of material is placed over the first piece and the leaflet mold. The first and second pieces of material are stitched to one another along at least a portion of the curved portion of the leaflet mold. The leaflet mold is removed from first and second pieces of material.

BRIEF DESCRIPTION OF THE DRAWINGS

The present invention will be further explained with reference to the appended Figures, wherein like structure is referred to by like numerals throughout the several views, and wherein:

FIGS. 18 and 19 are top views of bottom and top mold templates, respectively, of a plate assembly of the invention;

FIGS. 20 and 21 are top views of additional embodiments of bottom and top plates, respectively, of a plate assembly of the present invention;

FIGS. 22 and 23 are top views of additional embodiments of bottom and top plates, respectively, of a plate assembly of the present invention;

DETAILED DESCRIPTION

Figure 1A:
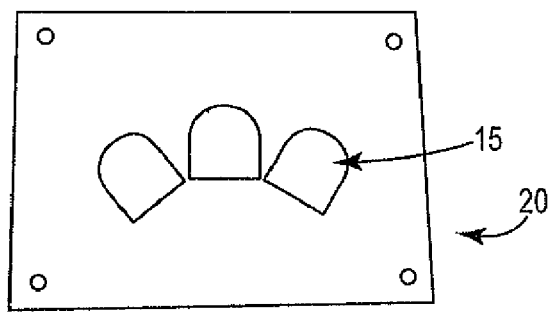
FIG. 1a is a top view of a plate having etched areas to which leaflet molds can be attached.

The prosthetic heart valves of the invention may be used for the replacement of pulmonary valves, aortic valves, mitral valves, or tricuspid valves. Alternatively, the prosthetic valves of the invention may be used to replace a failed bioprosthesis, such as in the area of an aortic valve or mitral valve, for example. At least one relatively flat sheet of material, such as pericardial tissue, is obtained for use in the construction of a prosthetic valve of the type described herein. This sheet of material can be obtained from a bovine heart, for example. Other donor species may alternatively be used, such as porcine tissue. Alternatively, a manufactured sheet of material may be used, such as a polymeric material sheet or a bio-engineered film. If pericardial tissue is used, it may be at least partially fixed or cross-linked with a buffered gluteraldehyde solution at some point during the assembly process in order to make the material easier for an operator to handle and manipulate. The shape, size, and configuration of the leaflet(s) and outer tubular portion of the prosthetic valve can specifically be designed and chosen for the type of valve that is being produced. In various embodiments of the prosthetic valves of the invention, three shaped leaflets are used; however, alternative embodiments of the prosthetic valves of the invention can include more than or less than three leaflets.

A prosthetic valve of the invention is intended to function substantially similar to a native or natural valve and also to function substantially similar to other prosthetic valves that are available to replace native or natural valves. In other words, the prosthetic valves of the invention have substantially similar design, flow and/or hemodynamic properties as a functional heart valve. For example, in the closed position, the leaflets of a prosthetic valve of the invention flex towards the valve annulus to seal the valve and prevent back-flow or leakage in the rearward direction. When in the open position, the leaflets of a prosthetic valve of the invention flex in such a way that they allow free flow of blood across the prosthetic valve. In certain embodiments of the prosthetic valves of the invention, the leaflets are shaped, such as by molding techniques, to provide coaptation angles that are substantially similar to a functional, native valve.

The prosthetic valves of the invention can include stented or stentless valves. In either case, the valves of some embodiments are compressible to a reduced diameter during the implantation process, such as for transcatheter valve implantation, and can be capable of being expanded to a larger diameter once they are in their desired implantation location.

The prosthetic valve assemblies of the present invention can include a stent and prosthetic heart valve as described herein, and can be used as a surgical sutureless or apical implant. The prosthetic valve assemblies also can be utilized in percutaneous replacement of cardiac valves, for example. As discussed herein, conventional methods of incorporating a prosthetic valve into a stent can in some cases lead to areas of concentrated stress at the points where the leaflets are attached to the stent frame. This can cause rips or tears in the leaflets and thus compromise the hydrodynamic performance of the valve. To minimize these areas of concentrated stress, the prosthetic valve assemblies of the invention can be made of durable synthetic materials and biological materials, wherein these materials are attached directly to the stent. One exemplary method for preparing a prosthetic valve assembly of the present invention, which is described in further detail below, generally includes the manufacture and preparation of a molded prosthetic valve onto which a cuff and/or sleeve is sewn. The valve can be fabricated from a biocompatible material such as polyester cloth or similar material. The molded prosthetic valve can then be mounted or attached to a stent. For example, in one embodiment of the invention, both a cuff and a sleeve are sewn onto a molded prosthetic valve, and then sewn directly to the stent. In other embodiments, the commissural points of a molded prosthetic valve are reinforced with a synthetic material, for example, an acetyl homopolymer such as polyoxymethylene (commercially available under the tradename "DELRIN"), and used to secure the valve to the stent. Other biocompatible, semi-rigid materials may alternatively be used. In certain embodiments of the methods of attachment, the components of the prosthetic valve constructed from biological tissue are not attached directly to the stent.

In addition to reducing leaflet stress, the use of the cuff and sleeve can also increase the strength of the prosthetic valve assembly. That is, sandwiching the stent between two cloth layers creates attachment points for the prosthetic heart valve assembly, and particularly creates such points for the areas of the prosthetic valve that are not in alignment with a stent strut or a node. Thus, the cuff and sleeve provide increased structural support for the prosthetic valve. Moreover, the cuff and/or sleeve can enhance the flexibility of the valve attachment sites during crimping and/or surgical distortion of the stent in certain embodiments of the prosthetic valve assembly of the invention, and can help to distribute stress more evenly around the circumference of the stent and valve assembly. The sleeve also creates a surface for continuous leaflet attachment points along the margin of attachment and commissures. The sleeve can also provide an annular gasket and promote healing, thus reducing the risks of paravalvular leakage and device migration.

In accordance with the invention, molds for shaping aortic, pulmonary, tricuspid and mitral replacement valves are also provided. Biological membranes, including autologous, homologous and heterologous tissue, such as pericardial tissue, and non-biological membranes, including polymeric membranes, are suitable to be used in the methods of the invention to form the prosthetic heart valves. One feature of one embodiment of the molds of the invention is that they include two thin templates having complementary surfaces that mate with one another. The joint mating surfaces of the two templates define the configuration and dimensions of the resulting prosthetic heart valve membrane.

Referring now to the Figures, wherein the components are labeled with like numerals throughout the several Figures, and initially to FIG. 1a, a plate 20 is illustrated, which includes multiple etched areas 15 to which leaflet molds can be attached. The thickness of the plate can be in the range of approximately 1/32 inch to 1/4 inch, although the thicknesses can be greater or less than this size range. The plate 20 can be manufactured from metallic materials, such as stainless steel, or from plastic materials, such as acrylic, high density polyethylene, polypropylene, polyesters, polyamides and other suitable plastic materials. The plate 20 can alternatively be made using plastic manufacturing techniques known in the art, such as injection molding, laser cutting, and the like. Plate 20 can have a substantially uniform thickness, although it is possible that its thickness varies at least somewhat across its length and/or width.

Figure 1B:
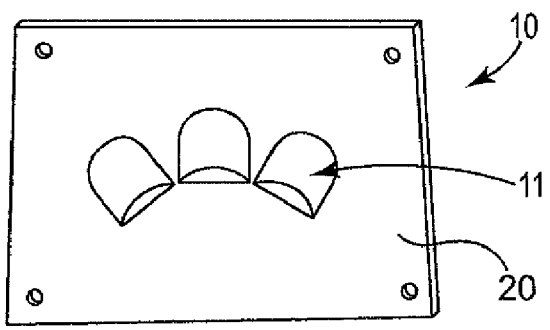
FIG. 1b is a perspective view of the plate of FIG. 1a with three attached leaflet molds.
Figure 2:
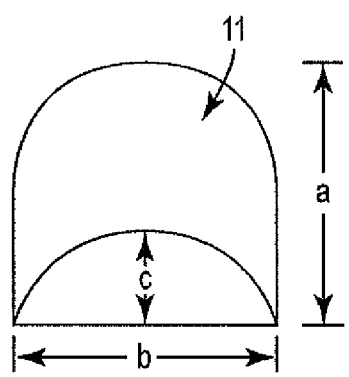
FIG. 2 is a schematic top view of one leaflet mold of the type shown in FIG. 1b.
Figure 3:
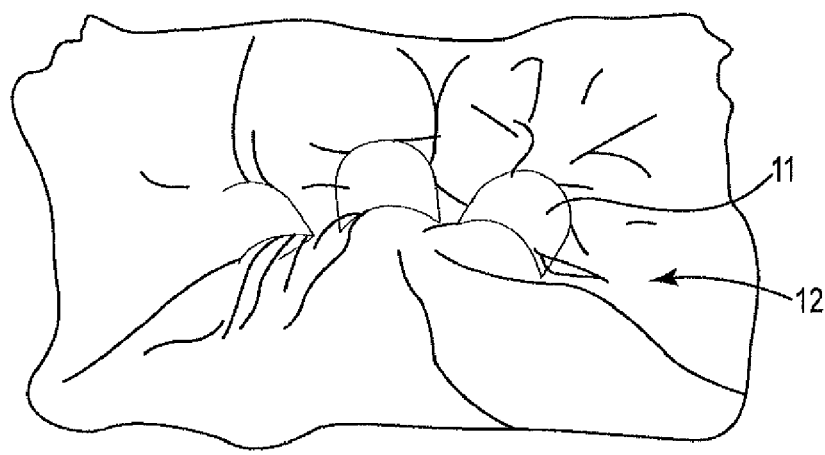
FIG. 3 is a perspective view illustrating the shaping of a prosthetic heart valve using the plate of FIG. 1b.
Figure 4:
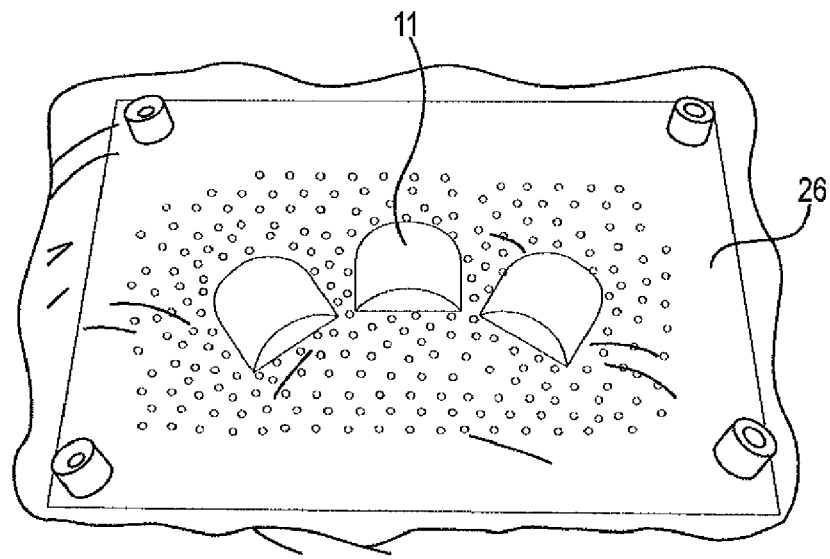
FIG. 4 is a perspective view illustrating the shaping of a prosthetic heart valve using the plate of FIG. 1b along with a top plate.

In one embodiment of the invention, plate 20 includes three etched areas 15, which are the areas on which three leaflets can be formed. With regard to FIG. 1b, a mold plate 10 is illustrated, which includes plate 20 with three attached leaflet molds or projections 11. The projections 11 are arranged along an arc on the plate 20. As shown in FIG. 2, each projection 11 includes dimensions a, b, and c, which define the shape and configuration of a leaflet of a prosthetic heart valve that will be prepared using the mold plate 10. As is further shown in FIG. 3, three shaped leaflets can be formed by placing a piece of tissue 12 (which may be pericardial tissue, for example) on the surface of the mold plate 10 from which the projections 11 extend. The pericardium or tissue material 12 can then be smoothed over the projections 11, if desired. Another plate 26, which includes three windows or openings that correspond with the size, shape, and positions of the leaflet molds 11, is then positioned relative to the projections 11 of mold plate 10, as is illustrated in FIG. 4. Mold plate 10, with its leaflet molds or projections 11, is designed to provide a prosthetic heart valve that is sized and shaped to be substantially similar to a corresponding functional native heart valve. For example, the leaflet molds 11 are sized, shaped and positioned to provide molded leaflets that will desirably be sized and shaped so that they contact each other when the valve is closed to ensure proper valve closure. Depending upon the embodiment of the mold of the invention, the plate 26 can include more than or less than three openings to correspond with the number of projections 11 extending from plate mold 10. Each opening in the plate 26 generally defines the perimeter of a projection 11 such that each projection 11 will extend through a corresponding opening when plate mold 10 and plate 26 are positioned relative to each other.

In accordance with the invention, leaflet molds of varying sizes may be provided to accommodate the anatomies of patients with varying heart valve root annulus dimensions. In fact, a single plate assembly can include leaflet molds that are the same or different sizes and shapes as other leaflet molds of that same plate assembly. In yet another alternative, a custom mold can be fabricated to provide a heart valve that is designed for a specific patient.

Figure 7:
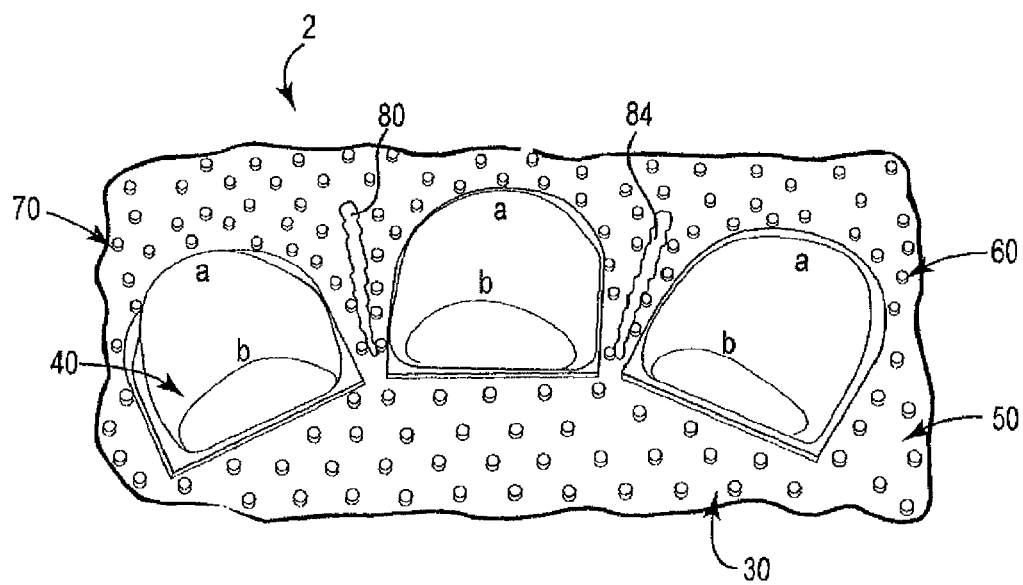
FIG. 7 is a perspective view of a portion of one embodiment of a forming plate of the invention for shaping a prosthetic heart valve.
Figure 8:
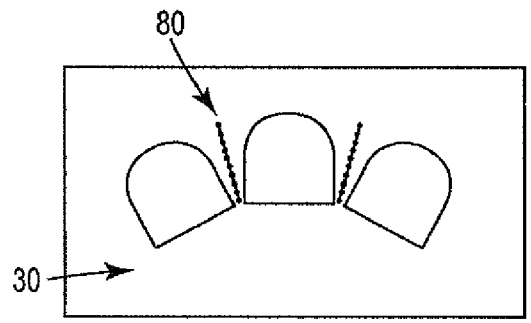
FIG. 8 is a top view of a bottom plate of a plate assembly of the invention.
Figure 9:
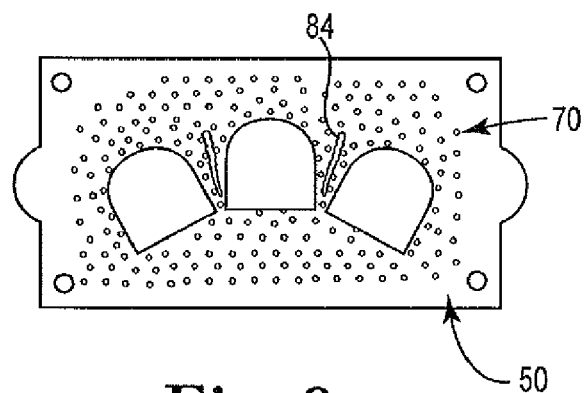
FIG. 9 is a top view of a top plate of a plate assembly of the invention.
Figure 10:
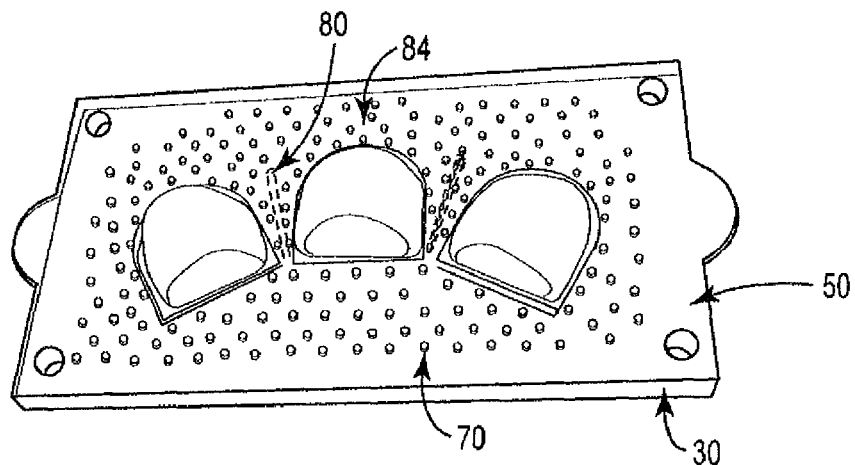
FIG. 10 is a perspective view of an embodiment of a plate assembly of the invention.

FIGS. 7-10 illustrate another embodiment of a mold of the invention. In particular, FIG. 7 is a perspective view of a mold assembly 2, which comprises a first template 30 and a second template 50 that is positionable on top of template 30. Template 30 includes multiple projections or leaflet molds 40 extending from one surface. As shown in FIGS. 7, 9, and 10, the generally planar portions of template 30 and/or template 50 can include multiple holes or perforations 70 that can allow a treatment or fixation solution to penetrate through the templates to a biological membrane 85 (shown in FIG. 11), when such a membrane or tissue is positioned between the templates 30, 50. In addition, mold assembly 2 includes at least one optional sewing guide 80, which is disposed on template 30 between adjacent projections 40, and a commissure support bar guide 84, which is a slot through the template 50 in the areas of the commissures. Each commissure support bar guide 84 is generally in alignment with a sewing guide 80 of template 30. When template 30 is positioned relative to template 50, a commissure support bar can rest on a membrane sandwiched between templates 30 and 50 in the area between leaflet molds. Thus, a commissure support bar can be sewn to the membrane via the sewing guide 80 in the template 30 at the points of the commissures.

FIGS. 18 and 19 are additional illustrations of the first and second templates 130, 150, respectively, of a mold assembly of the invention. In particular, the first template 130 includes a sewing guide 502 for attachment of a commissural post, a leaflet sewing guide 503 that corresponds with the outer shape and size of the openings 511 of template 50, and multiple projections 501. The projections or leaflet molds 501 extend from the template 130 to correspond to the openings 511 of the template 150.

FIGS. 20 and 21 illustrate components of another embodiment of a mold system or assembly of the invention. This mold assembly includes templates 600 and 610, and a leaflet sewing guide 603 that corresponds with the outer shape and size of the openings 611 of template 610. In this embodiment, the mold system or assembly does not include a sewing guide for the commissural posts.

FIGS. 22 and 23 illustrate yet another embodiment of components of a mold assembly of the invention. This mold assembly includes first and second templates 700, 710, a leaflet sewing guide 705 and a cuff sewing guide 704. In this embodiment, the mold system or assembly does not include a sewing guide for the commissural posts, although the assembly could optionally include such a sewing guide.

Figure 24:
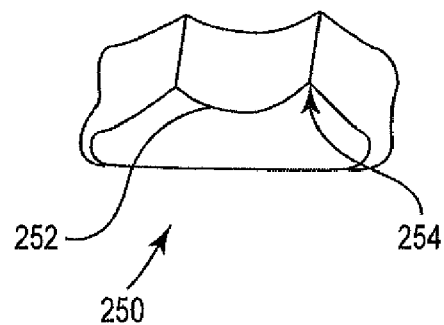
FIGS. 24-25 are perspective views of another embodiment of a mold of the present invention for use in shaping a prosthetic heart valve.
Figure 25:
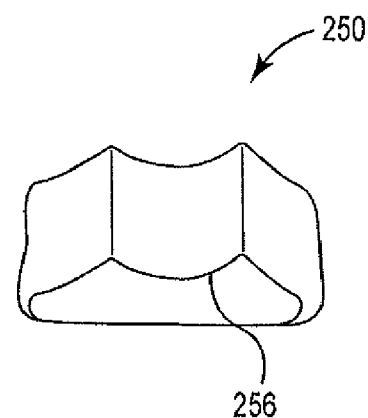
Figure 26:
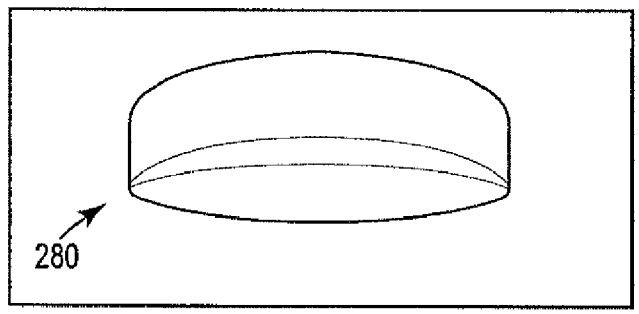
FIG. 26 is a schematic view of a template used for sewing of valve material.
Figure 27:
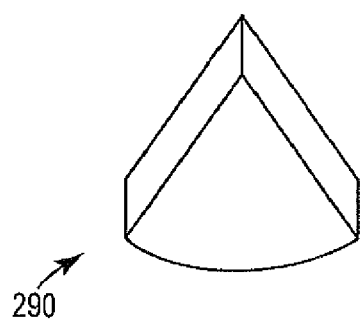
FIG. 27 is a perspective view of a shaping template.

FIGS. 24-25 illustrate yet another embodiment of a mold 250 of the invention. These figures illustrate a multiple piece mold system that can be prepared to mold biological tissue into a tube shape and/or a leaflet shape. Such shaping can occur prior or subsequent to sewing. The mold 250 of the present invention includes a feature having a curvature of center portion 252 that matches the valve tube wall. The dimensions of the curvature are dependent upon the tube size, number of desired leaflets and the like. The mold 250 includes edges 254 that are rounded or smoothed to minimize potential damage to the tissue. In certain embodiments, this mold 250 can be used as a sewing fixture. In one embodiment, pericardial tissue for the construction of the tube wall portion of the prosthetic valve is placed onto the mold 250. FIG. 25 illustrates a mold 250 for a leaflet in its closed position, wherein the contours of the top surface of a mold 256 follow that of a leaflet belly. This mold is made to sit on top of first layer of pericardial tissue (outer tube wall), where it is locked into place. A second layer of pericardium (the leaflet layer) can then be placed over the leaflet mold. An additional mold shaped as the negative of the inflow region can also be provided such that the contours of its top surface follow that of the leaflet margin of attachment. This template is made to sit on top of the second layer of pericardial tissue (leaflet) and locked into place. The relationship between the length of margin of attachment of the leaflet and the length of the side seam lines is maintained. FIG. 26 illustrates a sewing template 280, which includes a sewing insert to lift up the leaflet material away from the tube material. The shape of the sewing insert is non-specific, but it should hold the leaflet material up and away from the template. The edges of the insert also provide a sewing path. The tissue is placed into the mold for fixation, with the specifically shaped inserts designed to provide proper belly shape, coaptation angles, and the like. One example of a shaping insert 290 is illustrated in FIG. 27, which can be placed into the center curved portion of a mold, such as mold 250.

Figure 28:
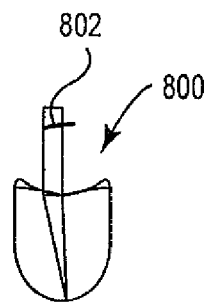
FIG. 28 is a top schematic view of another embodiment of a mold to shape leaflets of a pericardial valve.
Figure 29:
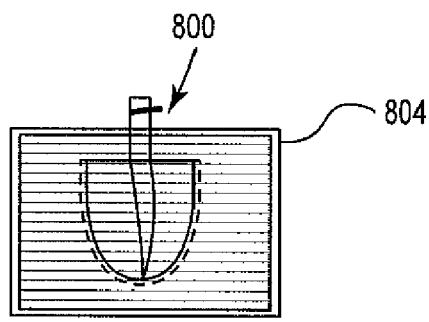
FIG. 29 is a top schematic view of the mold of FIG. 28 shown with sheets of pericardial material to form a leaflet.
Figure 30:
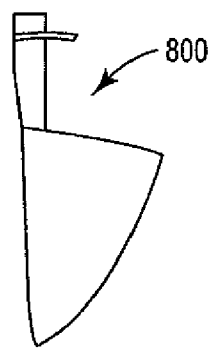
FIG. 30 is a side view of the mold of FIG. 28.

FIGS. 28-30 illustrate another embodiment of a mold 800 in accordance with the invention. Mold 800 can be one of a series of multiple molds that can be used to shape a corresponding number of leaflets. Each mold 800 includes a screw or other fastener 802 that can be used for alignment and securing of multiple molds relative to each other and relative to sheets of pericardial material. In one embodiment of the invention, partially fixed pericardium can be used for easy handling of the tissue during the preparation of the heart valve, although a fabric or another biocompatible material may instead be used. In any case, the sheet of material is placed on a clean surface, and a leaflet mold 800 is placed on top of this sheet of material. A second sheet of material (see material layer 804 in FIG. 29) is then positioned over the top of the mold 800. The material layers can then be stitched by first stitching along the edges, then around the mold to create one leaflet. The same process is repeated for each additional leaflet that is needed for a particular heart valve. All of the molds with the leaflets are then brought together, aligned at their tops, and held together by a screw or other fixation device. Any extra tissue can be pulled (other than the leaflet material), and seam stitches can be made. The entire valve can then be fixed, such as in a gluteraldehyde solution, with the leaflet molds in place to maintain the shape of the leaflets. The molds can then be removed and the valve can be attached to a stent, if desired. Alternatively, the valve will not be fixed until after it is attached to a stent.

The prosthetic heart valves of the present invention can be fabricated, at least in part, from a nonbiological membrane and/or a biological membrane, such as a mammalian tissue, of the type that can be obtained from humans, pigs, cows, and sheep, for example. Exemplary tissue for preparation of a prosthetic heart valve includes, for example, porcine aortic root tissue, porcine, equine, and/or bovine pericardium. Typically, such tissue is obtained directly from a slaughter house, and dissected at the slaughter house to remove undesired surrounding tissue. Either at the site of slaughter or shortly thereafter, but prior to significant tissue damage and/or degradation, the tissue is shipped on ice in order to reduce autolytic damage to the tissue and to minimize bacterial growth during shipment. The tissue is shipped and received within about 24 to 48 hours to a location where the tissue is thoroughly rinsed, for example, with a non-phosphate buffered organic saline solution. Following the rinse procedure, the tissue is placed into the mold, such as mold assembly 2 of FIG. 7, for example. The two templates 30 and 50 of the mold assembly 2 are joined together with fasteners, such as the exemplary fasteners 87, shown in FIG. 11. The tissue may thereby be held at four corners by fasteners 87 that consist of steel posts and silicone bands, for example. The tissue may be provided with holes that are pre-cut so that they can be placed over the posts. Silicone bands can be placed onto each post in order to keep the tissue seated. Instead of the fasteners 87, other mechanical devices such as clips, clamps, bolts, or springs can be used to hold the two templates together.

Figure 6:
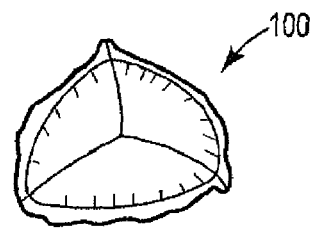
FIG. 6 is a top view illustrating the shaped prosthetic heart valve formed by the material of FIGS. 5a through 5d.

The mold assembly 2 having tissue sandwiched between the two templates 30 and 50 is then submerged in a fixation solution, such as a solution having glutaraldehyde, to cross-link the tissue. Cross-linking methods and solutions are well-known to the art. During submersion in the fixation solution, the solution percolates through the templates 30 and 50 to cross-link the tissue. Then, the mold is removed from the fixation solution, rinsed, and the tissue can be trimmed with a surgical knife or other trimming device along the edges of the mold assembly 2. Either prior or subsequent to removing the tissue from the mold, commissural posts may be reinforced using strips of a synthetic material, such as, for example, an acetyl homopolymer such as polyoxymethylene (commercially available under the tradename "DELRIN"). In addition, either prior or subsequent to removing the tissue from the mold, the commissural posts may be additionally reinforced using one or more strips of a biocompatible woven fabric, such as a polyester material, (e.g., polyester material commercially available from the DuPont Company under the trademark "DACRON"). After the trimmed tissue is removed from the mold assembly 2, the loose ends of the trimmed tissue can be attached to one another to form the heart valve 100, as is illustrated in FIG. 6, for example.

Figure 11:
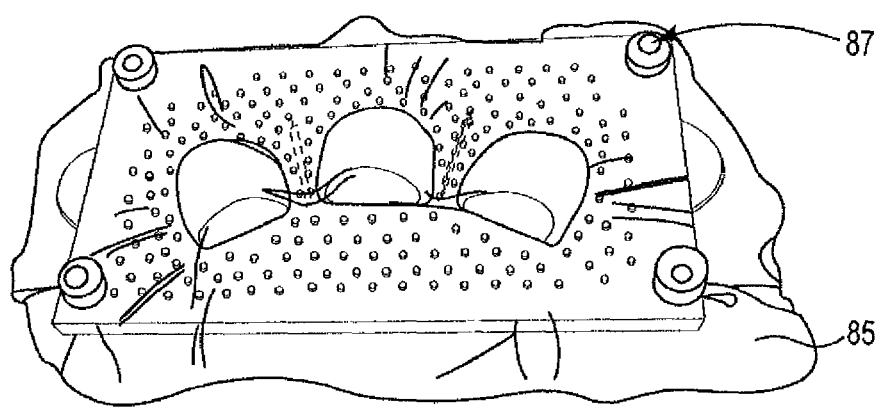
FIG. 11 is a perspective view illustrating the shaping of a prosthetic heart valve using the plate assembly components of FIGS. 7-10.
Figure 12:
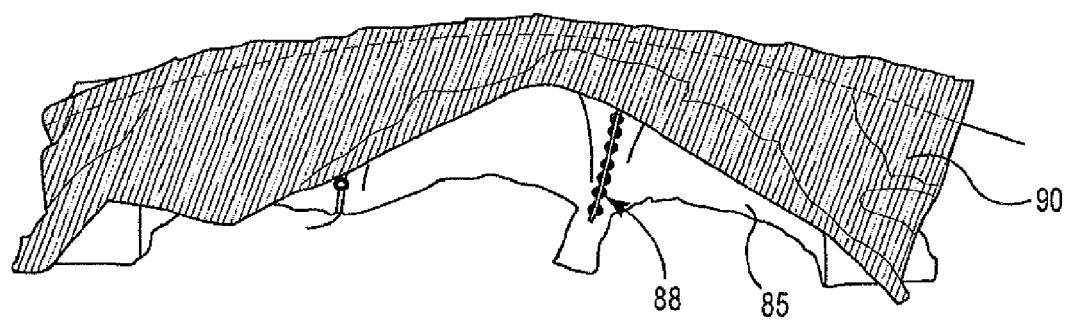
FIG. 12 is a perspective view illustrating the preparation of a prosthetic heart valve assembly of the invention.
Figure 13:
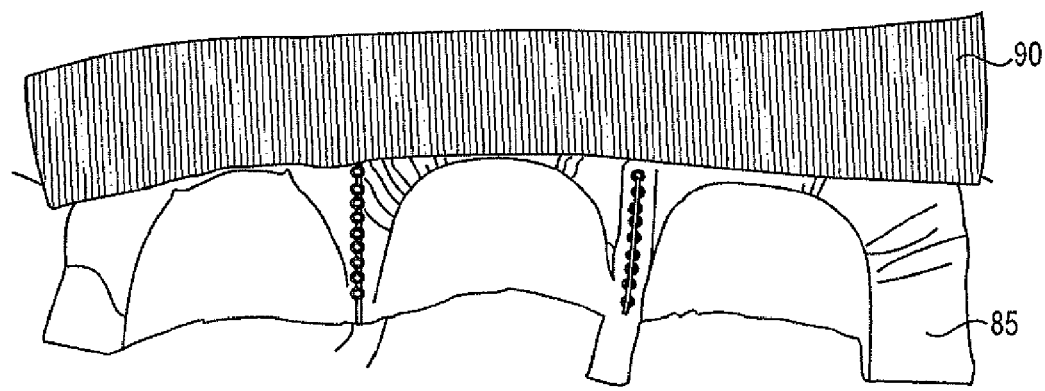
FIG. 13 is another perspective view further illustrating the preparation of a prosthetic heart valve assembly of the invention.

As discussed above, the prosthetic heart valves of the invention can include stented or stentless valves. In the case of one embodiment of a stented valve, once the trimmed tissue 85 (see FIG. 11) is removed from the mold assembly 2, a cuff 90 made of a biocompatible woven fabric, such as a polyester material is attached to the molded prosthetic valve, as is illustrated in FIG. 12. Alternatively, cuff 90 can be attached to the tissue prior to removing the molded prosthetic valve from the templates. For example, a cuff can be positioned between templates 700 and 710 of mold assembly of FIGS. 22 and 23, and then attached to the tissue via sewing a along cuff sewing guide 704.

As discussed herein, the prosthetic valve assemblies of the invention can be utilized in percutaneous replacement of cardiac valves, for example. One exemplary method for fabricating a stented valve for such delivery generally includes preparation of a shaped prosthetic valve, then a subsequent mounting or attachment of the prepared prosthesis to the stent, which are described below in further detail.

Figure 15:
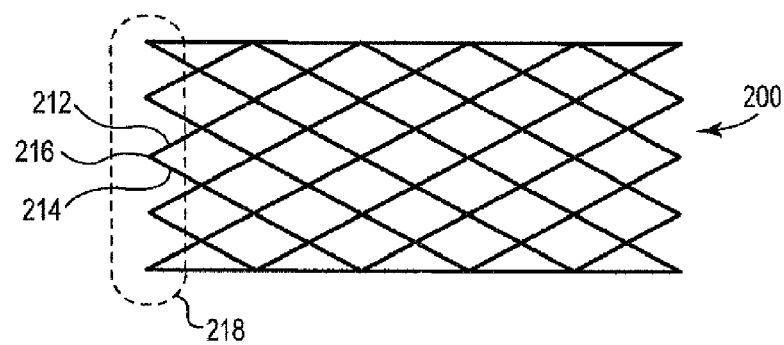
FIG. 15 is a front schematic view of one embodiment of a stent for a prosthetic heart valve assembly of the invention.

Turning now to FIG. 15, one exemplary embodiment of a stent 200 is shown, upon which a prosthetic valve of the invention may be attached to provide a prosthetic valve assembly. Stent 200, like many cylindrical stents, generally takes the form of a series of zig-zag ring structures, such as are indicated generally by reference number 218. The structures 218 are coupled longitudinally to one another to form a generally cylindrical-shaped structure, although structures 218 can form be arranged in an at least slightly oval or elliptical shape. Each ring structure 218 takes the form of a series of adjacent generally straight sections (e.g., straight sections 212, 214) which each meet one another at one end at a curved or angled junction (e.g., junction 216) to form a "V" or "U" shaped structure. For purposes of the present application, this structure will be referred to as a "V," and the included junction (e.g., junction 216) is referred to as the base of the "V." The relatively straight portions (e.g., straight sections 212, 214) of the stent between the bases of the "V"s, are referred to herein as the "arms" of the "V" or simply as "arms." While the angled junctions illustrated take the form of relatively sharply angled junctions, the "V" terminology is also intended to include more gradually curved junctions as well, such as might be shaped more like a "U" with arms that are angled away from each other at least slightly.

Stents of the type illustrated are generally sized to be in the 12 mm to 30 mm diameter range when expanded, and are configured so that the bases of the "V"s are in one embodiment spaced no further than about 8 mm from one another around the circumference of the stent. It should also be understood that although the ring structures are coupled to one another at the base of each "V" in the illustrated embodiment, stents employed according to the present invention may employ ring structures coupled to one another at fewer bases of their "V"s or coupled to one another by additional and/or different structures, such as longitudinal members of the type disclosed in U.S. Pat. No. 6,773,455 (Allen, et al.), U.S. Pat. No. 6,641,609 (Globerman) and U.S. Pat. No. 6,136,023 (Boyle). The invention also includes within its scope those stents in which wires are formed into zig-zags and wound spirally to produce a cylindrical structure, as in U.S. Pat. No. 6,656,219 (Wictor) or woven stents as disclosed in U.S. Pat. No. 4,655,771 (Wallsten).

Figure 14:
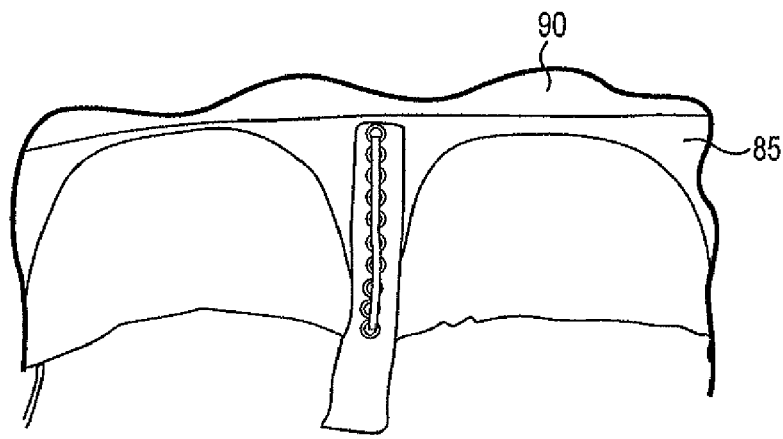
FIG. 14 is another perspective view illustrating the preparation of a prosthetic heart valve assembly of the invention.
Figure 16:
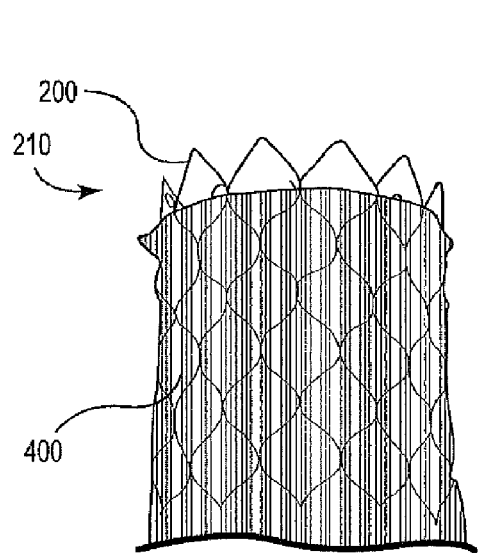
FIG. 16 is a front view further illustrating the attachment of a prosthetic heart valve to a stent in accordance with the invention.
Figure 17:
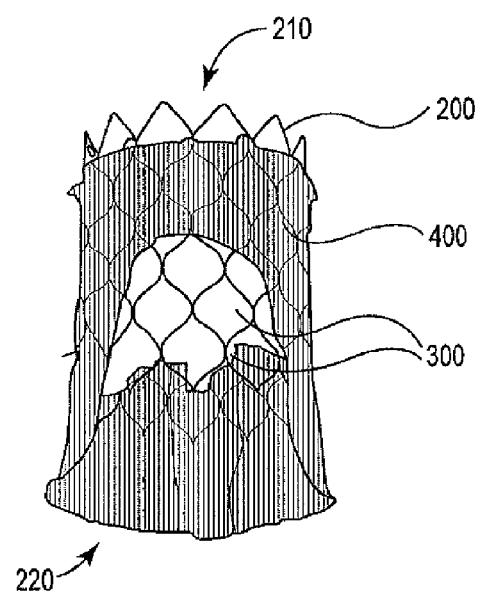
FIG. 17 is a back view of the stent and valve assembly of FIG. 16.

One exemplary method of mounting a prosthetic valve to a stent 200 is described with particular reference to FIGS. 16 and 17. The suturing procedure described herein may be performed on a mandrel or while simply manually holding a prosthetic valve 300. First, the stent 200 is placed over or around the prosthetic valve 300, and a sleeve 400 is placed over or around the stent. Sleeve 400 can be made of biocompatible material, such as a cloth, (e.g., Dacron). After the sleeve 400 is positioned as desired relative to the stent 200, an area of the sleeve 400 near an inflow end 210 is attached to the stent at cell nodes, struts, and/or strut intersections. Sleeve 400 is sutured to an area of the stent 200 nearest an outflow end 220, or along the struts of stent 200 at a location distal to the valve commissure (for example, see reference numeral 88 in FIG. 12). Sleeve 400 can also be sutured or attached to stent 200 near the inflow end 210. The attachment of sleeve 400 can be reinforced by suturing along the stent struts of some or all of the diamond shaped cells. The sleeve 400 may be scalloped into a "U" shape between each of the valve commissures (see FIG. 14) to reduce bulkiness in the area of the valve sinus and to provide clearance for the flow of blood.

Methods and techniques for incorporating the prosthetic valve and stent are known to the art. See, for example, U.S. Patent publication No. 2006/0206202, which is incorporated by reference herein. The suture material used for attachment may be visible to the human eye, such as by making the suture material of a color that is at least somewhat darker or lighter in color than the prosthetic valve 300 and/or the stent 200. For example, the suture material may be provided as a blue, 5.0 suture material. The suture material may be provided as a monofilament or multifilament structure made of natural or synthetic materials (e.g., nylon or polypropylene), or may alternatively include an elongated metal or metal-composite thread or filament or any other material that is suitable for permanently securing the stent to a prosthetic valve in accordance with the present invention.

In certain embodiments of fabricating the prosthetic heart valve assembly of the invention, the prosthetic heart valve is sewn to the stent such that all leaflets are on the same plane, which is perpendicular to the longitudinal axis of the stent. In certain embodiments of the invention, the prosthetic heart valve is sewn to the stent in such a way that the prosthetic valve does not extend beyond the inflow and/or outflow of the stent. In certain embodiments of the invention, the prosthetic heart valve is sewn to the stent in such a way that the valve commissures are at designated angles relative to each other around the circumference of the stent (e.g., 120 degrees from each other).

The invention will now be illustrated by the following non-limiting examples:

EXAMPLE 1

Three-Dimensional Leaflet Molding for a Prosthetic Aortic Valve

Materials:
Laboratory dental mold
Laser-cut acrylic fixation templates
Buffered Isotonic Gluteraldehyde (BIG; 0.2% gluteraldehyde)
10-minute quick-fixed (BIG) porcine pericardium
Methods:
Three individual molds of a closed leaflet from the outflow perspective were created using laboratory dental mold, such as is illustrated in FIG. 3. The molds have the shape of a leaflet that is laid flat such that the margin of attachment and commissures are on the same plane. The molds were positioned in an arched pattern, and the shape of the molds was laser etched into an acrylic plate. The etched areas positioned and held the clay leaflet molds in place, as is illustrated in FIGS. 1a and 1b.

Figure 5A:
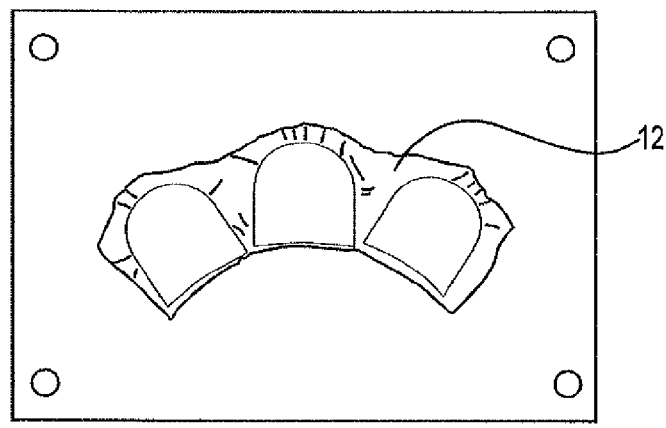
FIGS. 5a through 5d are perspective views illustrating the material used for shaping a prosthetic heart valve prepared using the plate of FIG. 1b.
Figure 5B:
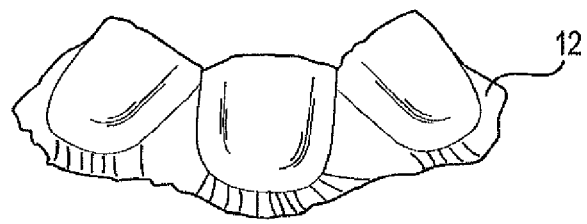
Figure 5C:
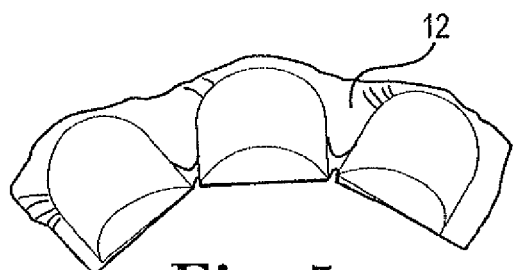
Figure 5D:
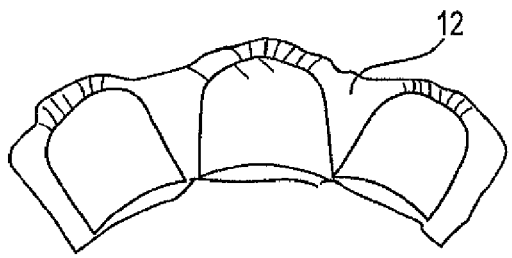

Porcine pericardial tissue 12 was "quick-fixed" (e.g., incubated for 10 minutes in BIG) and place over the leaflet mold, as is shown in FIG. 3. The tissue 12 was smoothed over the surface of mold and template, and wrinkles in the tissue were minimized. Next, the top acrylic template was placed over the tissue and molds and attached to the bottom template, as is illustrated in FIG. 4. This top template has three windows the size of the leaflet molds, and multiple 0.030" diameter holes that allow the gluteraldehyde solution to reach and cross-link the tissue. The tissue 12 was then further smoothed by pulling on the tissue edges, and fixed overnight in BIG. The top template was then removed, and the tissue 12 was hand-trimmed with scissors, as shown in FIGS. 5a-5c. The shaped tissue was then removed from the bottom template. As shown in FIG. 5d, the tissue 12 maintained its three-dimensional shape when removed from the templates.

Next, the leaflets were held in a folded configuration to simulate creating a valve. The leaflets appeared to close and assume a natural shape, as is illustrated in FIG. 6.

EXAMPLE 2

An Aortic Three-Dimensional Valve Assembly

A pericardial aortic valve assembly was prepared with a size 25 mm stent.

The valve leaflets coapted with minimal redundancy, and contained radio-opaque markers at the commissure tops and along the margin of attachment.

Materials:
Laboratory dental mold
Laser-cut acrylic fixation templates
Buffered Isotonic Gluteraldehyde (BIG; 0.2% gluteraldehyde)
10-minute fixed (BIG) porcine pericardium Methods:
Three leaflet molds were prepared having an increased leaflet size as compared to the molds used in Example 1. As shown in FIG. 7, mold material was added to increase the size of the leaflets in the belly (a) and in the free margin (b). In addition, as compared to Example 1, a location was created in the templates for tacking down the commissure posts, thereby facilitating assembly of the posts to the valve and stent (see FIGS. 7-10). Porcine pericardial tissue was fixed for ten minutes in BIG ("quick fixed") and laid over the surface of the mold, sandwiched between the templates, as is illustrated in FIG. 11, and immersed in BIG for a minimum of 12 hours.

After the tissue was fully fixed, additional posts (e.g., posts 88 of FIG. 12) were tacked in place. The tissue was then removed from the templates, and the inflow area was trimmed. A cuff made of Dacron cloth was sewn around the inflow area of the prosthetic valve, and a rectangular strip of Dacron cloth was sewn to the back of the commisures. To create the cuff, the cloth was laid on top of the tissue and attached by sewing along a stitch line approximately 2 mm up from the top of the margin of attachment. The cloth cuff was folded over stitch line in order to create a clean, smooth edge. As can be seen in FIG. 12, the post 88 lined up with the top of the commissure.

To attach the prosthetic valve to the stent, a cloth sleeve was sewn along the outside of the stent and scalloped (see FIGS. 16 and 17). The purpose behind this is to reduce paravalvular leakage, promote growth/host attachment, and to serve as an attachment point for the cuff and commissure posts. Attachment of the cuff to outer sleeve cloth rather than the stent will help with durability (because there will not be pulling against the sharp and rigid stent) and with extension during crimping (because cloth can absorb some of the elongation that occurs).

The prosthetic valve was then sewn into stent by attaching the inflow cuff area to the outer cloth sleeve, as is illustrated in FIG. 16. Then, the sleeve was scalloped in the sinus region, as is illustrated in FIG. 17. The scalloped edges of sleeve were then sewn to the stent, and radiopaque markers, such as barium impregnated silicone and metal figure-eights were added to the peak of the margin of attachment and the tops of the commissures, respectively.

EXAMPLE 3

A set of templates were prepared having a semi-circular stitch hole pattern around the leaflet molds, as is illustrated in FIGS. 18 and 19. The purpose of this was to prepare a template for shaping and sewing a defined leaflet shape. In Examples 1 and 2, the leaflet shape is defined by the molded shape of the tissue, but under pressure the tissue alone cannot hold/maintain the proper shape. When stitched, the semi-circular stitch hole pattern of the leaflet sewing guide 503 provided a solid shape definition.

EXAMPLE 4

As shown in FIGS. 20 and 21, a set of templates was prepared having modified stitch holes 603 around the leaflet molds to be fully circular and offset from leaflet mold. The purpose of this was to improve ease of assembly. In addition, the sewing guide for the commissural points was removed.

EXAMPLE 5

As shown in FIGS. 22 and 23, the templates shown in Example 4 were modified by adding a row of stitches 704 above the leaflet molds in order to stitch the cloth cuff to the prosthetic valve using the molding template. In Examples 1-4, the cloth cuff was added after removing the tissue from the templates. Attaching the cuff using this template pattern resulted in an increase in manufacturing speed and repeatability.

The present invention has now been described with reference to several embodiments thereof. The foregoing detailed description and examples have been given for clarity of understanding only. No unnecessary limitations are to be understood therefrom. It will be apparent to those skilled in the art that many changes can be made in the embodiments described without departing from the scope of the invention. Thus, the scope of the present invention should not be limited to the structures described herein, but only by the structures described by the language of the claims and the equivalents of those structures.

What is claimed is:

1. A method of forming a leaflet of a prosthetic valve, comprising the steps of:
   placing a first piece of material on a working surface with a first surface of the first piece of material facing generally outwardly;
   placing a bottom surface of a leaflet mold on the first surface of the first piece of material, wherein the leaflet mold further comprises a convex surface extending from the bottom surface, and an outer peripheral shape opposite the bottom surface that comprises a curved portion;
   placing a second piece of material over the first piece of material and the leaflet mold;
   stitching the first piece of material to the second piece of material along at least a portion of the curved portion of the outer peripheral shape of the leaflet mold; and
   removing the leaflet mold from the first and second pieces of material.

2. The method of claim 1, further comprising the step of fixing the first and second pieces of material with a fixation solution prior to removing the leaflet mold from the first and second pieces of material.

3. The method of claim 1, wherein the bottom surface is planar.

4. The method of claim 1, wherein the step of placing the second piece of material over the first piece of material includes placing the second piece of material over the convex surface of the leaflet mold.

5. The method of claim 1, wherein after the step of placing the second piece of material over the first piece of material and prior to the step of stitching the first piece of material to the second piece of material, the method further comprising:

placing a shaping insert over the second piece of material in a region of the curved portion.

6. The method of claim 5, wherein the step of placing a shaping insert over the second piece of material includes bringing a curved face of the shaping insert into contact with the second piece of material.

7. The method of claim 6, wherein the curved face terminates at a lateral edge, and further wherein the step of stitching the first piece of material to the second piece of material includes sewing the first and second pieces of material to one another immediately adjacent the lateral edge.

8. The method of claim 5, wherein prior to the step of stitching, the method further comprising:

placing a sewing template over the second piece of material;

wherein the sewing template provides a guide for stitching the first and second of pieces of material to one another.

9. The method of claim 8, wherein the step of placing the shaping insert includes an edge of the shaping insert holding a segment of the second piece of material away from the template.

10. The method of claim 1, further comprising forming a tube from the first piece of material.

11. The method of claim 10, further comprising forming a leaflet from the second piece of material.

12. The method of claim 1, further comprising placing a secondary mold shaped as a negative of a heart valve inflow region over the second piece of material.

* * * * *